(12) United States Patent
Kerrish et al.

(10) Patent No.: US 7,538,094 B2
(45) Date of Patent: *May 26, 2009

(54) COMPOSITION CONTAINING RIBAVIRIN AND USE THEREOF

(75) Inventors: Donald J. Kerrish, Wexford, PA (US); John R. Bergeron, Middletown, MD (US); Larry L. Augsburger, Severna Park, MD (US)

(73) Assignee: Three Rivers Pharmacueticals, LLC, Cranberry Township, PA (US)

( * ) Notice: Subject to any disclaimer, the term of this patent is extended or adjusted under 35 U.S.C. 154(b) by 101 days.

This patent is subject to a terminal disclaimer.

(21) Appl. No.: 10/882,358

(22) Filed: Jul. 2, 2004

(65) Prior Publication Data

US 2005/0019406 A1 Jan. 27, 2005

Related U.S. Application Data

(63) Continuation-in-part of application No. 10/665,728, filed on Sep. 22, 2003, now abandoned.

(60) Provisional application No. 60/411,747, filed on Sep. 19, 2002.

(51) Int. Cl.
*A01N 43/04* (2006.01)
*A61K 31/70* (2006.01)
*A61K 9/20* (2006.01)

(52) U.S. Cl. .................................. 514/43; 424/465

(58) Field of Classification Search .................. 514/43; 424/451, 464

See application file for complete search history.

(56) References Cited

U.S. PATENT DOCUMENTS

| | | | |
|---|---|---|---|
| 3,277,520 A | 10/1966 | Nakahara | |
| 3,798,209 A | 3/1974 | Witkowski et al. | |
| 3,927,216 A | 12/1975 | Witkowski et al. | |
| 3,948,885 A | 4/1976 | Witkowski et al. | |
| 3,976,545 A | 8/1976 | Witkowski et al. | |
| 4,138,547 A | 2/1979 | Christensen et al. | |
| 4,211,771 A | 7/1980 | Witkowski et al. | |
| 4,439,453 A | 3/1984 | Vogel | |
| 4,748,023 A | 5/1988 | Tamas et al. | |
| 5,405,837 A | 4/1995 | Weber | |
| 5,767,097 A | 6/1998 | Tam | |
| 5,914,128 A | 6/1999 | Liebowitz et al. | |
| 5,916,594 A | 6/1999 | Liebowitz et al. | |
| 6,051,252 A | 4/2000 | Liebowitz et al. | |
| 6,063,772 A | 5/2000 | Tam | |
| 6,110,498 A | 8/2000 | Rudnic et al. | |
| 6,130,326 A | 10/2000 | Ramasamy et al. | |
| 6,150,337 A | 11/2000 | Tam | |
| 6,172,046 B1 | 1/2001 | Albrecht | |
| 6,177,074 B1 | 1/2001 | Glue et al. | |
| 6,180,639 B1 | 1/2001 | Coates et al. | |
| 6,335,032 B1 | 1/2002 | Liebowitz et al. | |
| 6,337,090 B1 | 1/2002 | Liebowitz et al. | |
| 6,423,695 B1 | 7/2002 | Tam et al. | |
| 6,461,605 B1 | 10/2002 | Cutler et al. | |
| 6,472,373 B1 | 10/2002 | Albrecht | |
| 6,524,570 B1 | 2/2003 | Glue et al. | |
| 6,541,014 B2 | 4/2003 | Rudnic et al. | |
| 2003/0018000 A1 | 1/2003 | Kerrish et al. | |
| 2003/0104050 A1* | 6/2003 | Matharu et al. | 424/465 |
| 2006/0083785 A1 | 4/2006 | Kerrish et al. | |

FOREIGN PATENT DOCUMENTS

| | | |
|---|---|---|
| CA | 1261265 | 9/1989 |
| CA | 2135669 A1 | 5/1996 |
| EP | 0 707 855 A2 | 4/1996 |
| WO | WO-92/19227 | 11/1992 |
| WO | WO-96/36351 | 11/1996 |
| WO | WO-02/074317 A1 | 9/2002 |
| WO | WO-03/039517 A1 | 5/2003 |
| WO | WO 2004/026261 A2 | 4/2004 |

OTHER PUBLICATIONS

Botzolakis et al., "The Role of Disintegrants in Hard-gelatin Capsules", J. Pharm. Pharmacol. (1984) 36, 77-84.
Eggleston, M "Clinical Review of Ribavirin", Clinical Pharmacology of Antibiotics, Infection Control (1987) vol. 3, No. 5, pp. 215-218.
Fernandez et al., "Ribavirin: A Clinical Overview", European Journal of Epidemiology (1986) vol. 2, No. 1, pp. 1-14.
Hahn, F.E. "Mechanism of Action of Antieukaryotic and Antiviral Compounds", in: Hahn, F.E., *Antibiotics* (1979) pp. 439-458 (Springer-Verlag, New York, vol. V, Part 2).
Lachman et al., "Theory and practice of Industrial Pharmacy," (1986) pp. 66-68 (Lea & Febiger—Philadelphia).
Longer et al., Remmington's Pharmaceutical Sciences, entitled, "Sustained-Release Drug Delivery Systems," (1990) pp. 1676-1693, (Mack Publ. Co., Easton, PA).
O'Connor, PhD et al., Pharmaceutical Sciences, entitled, "Powders," (1990) pp. 1615-1632.
Ormos, Z.D. "Granulation and Coating" in: Chulia et al., ed. *Powder Technology and Pharmaceutical Processes* (1994) pp. 359-376 (New York, Elsevier).
Merck Index—An Encyclopedia of Chemicals, Drugs, and Biologicals, Eleventh Edition, Budavari, ed. (1989) p. 1304.
Parikh, D. M. ed., *Handbook of Pharmaceutical Granulation Technology*, Chapters 1, 2, 11 (1997) pp. 1-23 and 333-368.
Parrott, Journal of Pharmaceutical Sciences, entitled, "Densification of Powders by Concavo-Convex Roller Compactor," Aug. 28, 1980.
Porter, Remington's Pharmaceutical Sciences, "Sustained-Release Drug Delivery System", Chapter 90 (1990) pp. 1666-1675.

(Continued)

*Primary Examiner*—Traviss C McIntosh, III
(74) *Attorney, Agent, or Firm*—McDermott Will & Emery LLP (57) ABSTRACT

Ribavirin formulations are disclosed for use in capsules or tablets as well as processes for their preparation and methods for their administration.

26 Claims, 3 Drawing Sheets

OTHER PUBLICATIONS

Prusiner et al., "The Crystal and Molecular Structures of Two Polymorphic Crystalline Forms of Virazole (1-β-D-Ribofuranosyl-1,2,4-triazole-3-carboxamide). A New Synthetic Broad Spectrum Antiviral Agent", Acta Cryst. (1976). B32, 419, pp. 419-426.

Ravin et al., Remmington's Pharmaceutical Sciences, entitled, "Preformulation," (1990) pp. 1435-1450, (Mack Publ. Co., Easton, PA).

Rudnic et al., Remmington's Pharmaceutical Sciences, entitled, "Oral Solid Dosage Forms," (1990) pp. 1633-1675 (Mack Publ. Co., Easton, PA).

Sidwell et al., "Broad-Spectrum Antiviral Activity of Virazole: 1-β-D-Ribofuranosyl-1,2,4-triazole-3-carboxamide", Science (Aug. 25, 1972) vol. 177, No. 4050, pp. 705-706.

Sidwell et al., "Ribavirin: An Antiviral Agent", Pharmac. Ther. (1979) vol. 6, pp. 123-146.

U.S. Appl. No. 10/285,188 Amendment Filed in PTO on Aug. 3, 2005 therefrom.

ICN Pharmaceuticals Inc. v. Three Rivers Pharmaceuticals, LLC—101 Fed. Appx. 335, 2004 U.S. App. LEXIS 12821 (Fed Cir. 2004).

ICN Pharmaceuticals, Inc. v. Geneva Pharmaceuticals Technology Corp., et al., 272 F. Supp. 2d 1028. (C.D. Cal. 2003) 12024.

James I. Wells, Pharmaceutical Preformulation: The Physicochemical Propoerties of Drug Substances, 1988, Chapter 7, pp. 209-214Ellis Horwood Ltd., England.

Leon Lachman, et al.—The Theory and Practice of Industrial Pharmacy, Third Edition, Indian Edition, Varghese Publishing House, Dadar Bombay, 1987, pp. 66-99.

Liebowitz et al File wrapper for U. S. Patent No. 6,335,032 issued Jan. 2002.

Bowen Declaration in file wrapper for U. S. Patent No. 6,335,032.

Liebowitz et al File wrapper for U. S. Patent No. 6,337,090 issued Jan. 8, 2002.

Bowen Declaration in file wrapper for U. S. Patent No. 6,337,090.

* cited by examiner

FIG. 1

| VESSEL NUMBER | % LABEL CLAIM OF RIBAMUNE™ 200-mg CAPSULES, LOT # 1A2738 | | | |
|---|---|---|---|---|
| | 15 MINUTES | 30 MINUTES | 45 MINUTES | 60 MINUTES |
| 1 | 100 | 101 | 101 | 101 |
| 2 | 98 | 98 | 97 | 98 |
| 3 | 98 | 98 | 98 | 98 |
| 4 | 98 | 100 | 98 | 98 |
| 5 | 97 | 97 | 97 | 97 |
| 6 | 96 | 97 | 96 | 97 |
| 7 | 96 | 95 | 96 | 96 |
| 8 | 96 | 96 | 96 | 96 |
| 9 | 95 | 96 | 96 | 95 |
| 10 | 97 | 97 | 98 | 97 |
| 11 | 95 | 95 | 95 | 94 |
| 12 | 94 | 95 | 95 | 95 |
| AVERAGE | 97 | 97 | 97 | 97 |
| %RSD | 1.7 | 2.0 | 1.7 | 1.9 |
| RANGE | 6 | 6 | 6 | 7 |

FIG. 2

| VESSEL NUMBER | % LABEL CLAIM OF REBETOL® 200-mg CAPSULES, LOT # ORCJ184 | | | |
|---|---|---|---|---|
| | 15 MINUTES | 30 MINUTES | 45 MINUTES | 60 MINUTES |
| 1 | 96 | 97 | 97 | 98 |
| 2 | 98 | 100 | 100 | 100 |
| 3 | 104 | 105 | 105 | 103 |
| 4 | 102 | 103 | 103 | 104 |
| 5 | 87 | 89 | 90 | 90 |
| 6 | 90 | 94 | 93 | 93 |
| 7 | 97 | 100 | 100 | 101 |
| 8 | 97 | 106 | 106 | 106 |
| 9 | 97 | 99 | 99 | 99 |
| 10 | 86 | 90 | 91 | 91 |
| 11 | 102 | 103 | 104 | 104 |
| 12 | 96 | 98 | 96 | 96 |
| AVERAGE | 96 | 99 | 99 | 99 |
| %RSD | 6.0 | 5.5 | 5.5 | 5.4 |
| RANGE | 18 | 17 | 16 | 16 |

FIG. 3

COMPOSITION CONTAINING RIBAVIRIN AND USE THEREOF

CROSS REFERENCE TO RELATED APPLICATION

This application is a continuation-in-part of application Ser. No. 10/665,728, filed Sep. 22, 2003 now abandoned, which claims the benefit of U.S. Provisional Application No. 60/411,747, filed Sep. 19, 2002. Both applications are hereby incorporated herein by reference. This application contains subject matter that may be similar to application Ser. No. 09/812,024, filed Mar. 19, 2001, now U.S. Pat. No. 6,720,000 B2.

TECHNICAL FIELD

The present invention relates to a pharmaceutical dosage of ribavirin. More specifically, the present invention relates to a process and product containing a ribavirin composition and its administration.

BACKGROUND

Ribavirin (1-β-D-ribofuranosyl-1H-1,2,4-triazole-3-carboxamide) is a known synthetic nucleoside analog with broad spectrum antiviral activity. See, e.g., U.S. Pat. No. 3,927,216 to Witkowski et al. It is a colorless, water-soluble, stable material and is known to have two polymorphic forms.

Ribavirin compositions are also known as, for example, disclosed in U.S. Pat. No. 6,337,090; Canadian Patent No. 2,135,669; and U.S. Patent Application Publication 20030104050 A1. As noted in U.S. Pat. No. 6,337,090, there are many processing difficulties in preparing ribavirin compositions, including flowability, uniformity, etc. Ribavirin is known to have poor flow, which adversely affects its manufacture into solid dosage forms. A drug's manufacturing characteristic is important because it can affect weight variability, uniformity etc. of a dosage form of the drug, which in turns affects the drug's dissolution and bio-availability in a subject having ingested it.

Ribavirin is currently indicated for use as a combination therapeutic for Hepatitis C. As such, ribavirin is administered in large dosages, e.g., a dose as large as 1200 mg per day, together with interferon injections. Currently, however, ribavirin is only approved in the United States in the form of a 200 mg dosage. Hence, dosing regimens involve 4 to 6 capsules a day for treatment of Hepatitis C infections. The multiple capsules are typically taken twice daily so that the proper level of ribavirin can be maintained in the body. This dosage regimen is continued daily for a number of months and because of the frequency and number of capsules required for treatment, patient compliance becomes problematic. Additionally, the large dose of ribavirin needed for treating Hepatitis C causes undesirable side-effects for some patients.

Accordingly, a need exists to ameliorate the dosage regiment so that a more stable concentration of ribavirin can be achieved in a subject taking the medicament and to facilitate patient compliance. A continuing need also exists for improved ribavirin compositions.

SUMMARY OF THE DISCLOSURE

An advantage of the present invention is a process and product containing an improved ribavirin composition that can be manufactured in solid dosage forms, e.g., immediate release or sustained release products.

These and other advantages are satisfied, at least in part, by a process of forming a free flowing granular ribavirin composition. The process comprises mixing ribavirin with at least one excipient to form a mixture; adding water to the mixture; forming the wet mixture into ribavirin containing particles; and drying the particles to form free flowing particles.

The free flowing ribavirin composition of the present invention advantageously allows the manufacture of highly uniform ribavirin dosages for immediate or sustained release of ribavirin when ingested in a human subject. By providing a free flowing composition, ribavirin dosages can be fabricated where the quantity of the composition varies only minimally among the produced dosage forms, e.g., the weight variation among produced capsules or tablets is minimal. The present inventive process also advantageously allows the manufacture of ribavirin dosages having high content uniformity, e.g., where the amount of the active ingredient among produced dosages varies minimally, which in turn leads to a consistent release of the drug when the composition is ingested.

Embodiments of the present invention include mixing at least one filler, at least one disintegrant, and at least one binder with ribavirin to form the mixture; adding about 15 wt % to about 80 wt % of water to granulate the mixture; forming ribavirin containing particles by milling or spheronizing the granulated mixture; drying the particles by heating the particles to a temperature ranging from about 25° C. to about 55° C., e.g., from about 35-45° C., until the particles contain a moisture content ranging from about 0.5% to 5.0%. The formed composition can then be used in the manufacture of capsules, tablets, etc.

Another aspect of the present invention is a process for preparing a sustained release ribavirin formulation. These formulations can be used as sustained release capsules and tablets. The sustained release composition can advantageously be taken with conventional immediate release ribavirin dosage forms or can be taken alone and can ameliorate some of the issues relating to an immediate release ribavirin dosage.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

BRIEF DESCRIPTION OF THE DRAWINGS

Reference is made to the attached drawings, wherein.

DETAILED DESCRIPTION OF THE DISCLOSURE

The present invention relates to preparing improved ribavirin compositions that can more readily be manufactured into ribavirin dosages for human ingestion. In one aspect of the present invention, ribavirin is prepared as a free flowing composition, e.g., a granular powder comprising loose particles or pellets, which advantageously allows the manufacture of highly uniform ribavirin dosages. The ribavirin compositions of the present invention also advantageously have a highly uniform compositional content thereby providing a uniform and consistent rate of release of the ribavirin when ingested by a human.

In practicing embodiments of the present invention, ribavirin is mixed with at least one excipient to form an initial mixture. The mixture is then reduced to particles or pellets, and, if needed, dried to form ribavirin containing particles.

The ribavirin compositions of the present invention can be prepared with any excipient, such as at least any one of a filler, diluent, disintegrant, binder, etc., which is physically and chemically compatible with ribavirin. The relative amount of ribavirin and other components in the composition will depend on the desired dosage. It is preferred that the composition contains a maximum amount of ribavirin, e.g., at least about 70% by weight.

Any filler or diluent can be used in the composition to provide bulk to the ribavirin composition, which is physically and chemically compatible with ribavirin. Examples of suitable fillers and diluents include lactose anhydrous, microcrystalline cellulose, starch, pregelatinized starch, modified starch, dibasic calcium phosphate dihydrate, calcium sulfate trihydrate, calcium sulfate dihydrate, calcium carbonate, lactose, dextrose, sucrose, mannitol, sorbitol, and their pharmaceutically acceptable salt or hydrate thereof, as appropriate. A combination of fillers and diluents can also be used. Preferred fillers and diluents are lactose monohydrate and microcrystalline cellulose.

The amount of filler in the compositions of the invention is preferably from about 0.5 to about 30 weight percent, based on the total weight of the ribavirin composition, e.g., from about 5 to about 20 wt %.

Any disintegrant that is chemically and physically compatible with ribavirin can be used in the composition. Examples of suitable disintegrants include croscarmellose, sodium starch glycolate, corn starch, pregelatinized starches, polacrillin potassium, polyacrylates such as Carbopol, sodium carboxymethyl cellulose, potato starch, microcrystalline cellulose, cross-linked polyvinylpyrrolidone, magnesium aluminium silicate, bentonite, alginic acid and alginates, or their pharmaceutically acceptable salt or hydrate thereof, as applicable. A combination of disintegrants may also be used. A preferred disintegrant is croscarmellose sodium.

The amount of disintegrant in the compositions of the invention is preferably from about 0.5 to about 20 weight percent, based on the total weight of the ribavirin composition, e.g., from about 1 to about 10 wt %.

Any binder that is chemically and physically compatible with ribavirin can be used in the composition. Examples of suitable binders include starches, e.g., potato starch, wheat starch, corn starch; gums such as gum tragacanth, acacia gum, and gelatin; microcrystalline cellulose, e.g., products known under the registered trademarks Avicel, Filtrak, Heweten or Pharmacel, hydroxypropyl cellulose, hydroxyethyl cellulose, and hydroxypropylmethyl cellulose; and polyvinyl pyrrolidone, e.g., Povidone.

The amount of binder in the compositions of the invention is preferably from about 0.5 to about 20 weight percent, based on the total weight of the ribavirin composition, e.g., from about 1 to about 10 wt %.

Other excipients that can be combined with ribavirin include hydroxypropyl cellulose, hydroxypropylmethyl cellulose, etc. In addition to excipients such as fillers, disintegrants, binders, etc. the ribavirin composition can also include a lubricant. Any pharmaceutically acceptable solid or liquid lubricant can be used in the composition, which is chemically and physically compatible with ribavirin. Typically the lubricant is used to enhance the flow and prevent sticking of the ribavirin composition. Suitable lubricants include magnesium stearate, calcium stearate, zinc stearate, talc, propylene glycol, polyethylene glycol, stearic acid, vegetable oil, sodium benzoate, sodium lauryl sulfate, magnesium lauryl sulfate, mineral oil, and polyoxyethylene monostearate as well as other salts and hydrates thereof. A combination of lubricants can also be used. A preferred lubricant is magnesium stearate.

The amount of lubricant in the compositions of the invention is preferably from about 0.1 to about 5 weight percent, based on the total weight of the ribavirin composition.

As is known in the art, bulk ribavirin is a poor flowing compound. It is a flaked material in bulk, which likely contributes to its poor flow. One way to quantify the flowability of a material is to measure its Carr Index. Typically, a material with a Carr index of greater than 25% is considered to have poor flow. (See, e.g., J. I. Wells, "Pharmaceutical Preformulation: The Physicochemical Properties of Drug Substances," Halstead Press div John Wiley & Sons, NY, 1988). A material with a Carr Index of 16-12% is considered to have good flow. Bulk ribavirin has a Carr Index typically around 50-42%. Dry blending a ribavirin mixture resulted in a Carr Index of 33%. Both bulk ribavirin and dry blending a ribavirin mixture have poor flow as measured by their Carr Index.

Another measure of flowability can be made by determining a material's angle of repose. The angle of repose is a standard test in the pharmaceutical industry to establish the relative flowability of a solid pharmaceutical formulation. (See, e.g., Lachman et al., "The Theory and Practice of Industrial Pharmacy" 3rd Ed. (1986) pp 67-68). A greater angle of repose means a less flowable material. Remington's Pharmaceuticals Sciences lists the angle of repose for glass beads (a high flowing material) at 23 degrees and for granular limestone (a poor flowing material) at 64 degrees. Cohesive materials can be as high as 90 degrees. (See Remington's Pharmaceutical Sciences, 19th Ed. Mack Publishing Co., (1995) p. 1607).

Based upon experimentation and investigation, it was determined that ribavirin compositions can be prepared having superior free flowing characteristics, e.g., having an angle of repose no higher than about 35 degrees, e.g., no higher than about 30 degrees. In one aspect of the present invention, a free flowing granular ribavirin composition can be prepared by wet granulating and drying a ribavirin mixture.

Any pharmaceutically acceptable wetting agent can be used to wet granulate a ribavirin mixture in preparing a ribavirin composition. Suitable wetting agents include water, esters, such as ethyl acetate, ketones, such as acetone, alcohols, such as methanol, ethanol, isopropanol, butanol, and combinations thereof. In one embodiment of practicing the present invention, the wetting agent is added to a ribavirin mixture in an amount of about 15 wt % to about 80 wt %. e.g.

from about 40 wt % to about 80 wt % based on the total weight of the mixture. Another way to describe the amount of wetting agent added to the mixture is based on the ratio of wetting agent to the dry mixture prior to granulation. Hence, adding about 15-80 wt % of a wetting agent based on the total weight of the mixture can also be characterized as adding a wetting agent in an amount between about 25% to about 400% based on the dry ingredients.

While suitable wetting agents can be used in preparing ribavirin compositions of the present invention, it has been discovered that water appears to impart better uniformity to the resulting composition. It is believed that water facilitates the content uniformity of a ribavirin mixture by partially dissolving some of the components, such as ribavirin itself, thereby homogeneously distributing the components during granulation with water. When the water is removed, as by evaporation and/or heating, the components tend to bind together thereby resulting in a homogeneous composition. While A second approach would be to administer one 600-mg ribavirin dose as the current capsule product and administer a second 600-mg dose as a delayed-release (i.e., enteric coated) formulation by coating a selected sieve cut (e.g., a −16+25 or −25+40) of the current pellets with an enteric polymer such as Eudragit RL or Surelease. Since the surface area-to-weight ratio of the pellets depends on their size, it would be preferred to use a narrow sieve cut for the delayed release formulation. This formulation would comprise of three 200-mg immediate-release capsules and three 200-mg delayed release capsules. The lag time, before the second (delayed release) dose is released, can be modulated by varying the coating level of the enteric polymer. Two different capsule colors can be used for the immediate- and delayed-release capsules; and three immediate and three delayed-release capsules can be filled in a pouch or sachet as one daily dose.

Another approach would be to administer two 600-mg ribavirin tablets, one an immediate-release tablet and the other a delayed-release tablet (i.e., immediate-release tablet coated with an enteric polymer). The current pellet process with or without the extrusion and spheronization steps can be used for the tablet product. A lubricant such as magnesium stearate may need to be included in the formula. A colorant can be added to the delayed-release tablet to distinguish it from the immediate-release tablet. One immediate-release and one delayed-release tablet can be packaged in a sachet as one daily dose. Alternatively, the immediate and delayed release tablets can be combined into a single tablet or equivalent dosage form.

Controlled release technologies useful for capsule and tablet formulations involve diffusion and matrix type systems. The present invention contemplates the use of coated particles containing ribavirin to delay the release of the drug as well as coated dosage forms to delay release of the drug. For the diffusion type system, a membrane or film (e.g., Ethocel or Eudragit R) is applied on top of a pellet or granule, as is known in the art. The gastrointestinal fluid enters the membrane, dissolves the drug in the pellet, and the dissolved drug molecules slowly diffuse through the membrane at a rate depending on the characteristics of the membrane and the dissolving drug. In a matrix system, the drug is mixed with a polymer (e.g., Methocel, guar gum, alginic acid, etc.) or a waxy material (e.g., bees wax, carnauba wax, etc.) and then granulated and compressed into tablets. These tablets would not disintegrate, but instead, swell and erode slowly (hydrophilic polymers), or remain intact in the case of a wax matrix. The drug dissolves in the matrix and slowly diffuses through the channels within the matrix. By optimizing the drug/polymer or drug/wax ratio and selecting the appropriate polymer or a mixture of polymers, a desired drug release can be achieved, as is known in the art. The present invention also contemplates the use of erosion tablets, i.e., those that do not disintegrate, but simply erode over time upon ingestion.

These systems are used for drugs with relatively short biological half-lives, since the amount of drug being eliminated from the body needs to be continuously replaced by the drug being released from the pellet or tablet at a controlled rate. Because of the relatively long biological half-life of ribavirin, a slow continuous release may not be appropriate for ribavirin. However, it can be optimized with such systems nonetheless. A combination of immediate- and delayed-release systems is also considered suitable for ribavirin dosing.

There are several formulas that can be utilized to produce ribavirin pellets by wet granulation, preferably with extrusion and spheronization. Table 1 describes a ribavirin formulation that can be used in preparing ribavirin pellets. The percent ranges of the formula are approximate and can vary depending on the particular amount of active ingredient needed in the dosage form as well as the type of dosage form used. The excipients are also approximate and depend on the type of dosage form.

TABLE 1

| Formulation Ingredient | % Total Formulation (wet)[1] | Function in the Formulation |
|---|---|---|
| ribavirin, U.S. Pharmacopeia Grade ("USP") | 40-80 | Active Pharmaceutical Ingredient |
| microcrystalline cellulose | 10-30 | Binder/Diluent |
| croscarmellose sodium | 2-6 | Disintegrant |
| polyethylene glycol | 5-20 | Binder |
| povidone | 1-4.5 | Binder |
| water U.S. Pat. No. | 15-50 | Wetting Agent[2] |

[1]Calculated on a wet basis.
[2]The wetting agent is removed from the formulation.

The dry ingredients listed in Table 1 above are mixed together and granulated with the wetting agent, extruded through a screen (0.4 mm to 1.0 mm), spheronized, and fluid bed dried. Although polyethylene glycol was used in the formulation, it was discovered that its use resulted in a ribavirin composition having poor characteristics for capsule formation. It was observed that a ribavirin composition prepared with polyethylene glycol caused a capsule containing the composition to become brittle over time. It is believed that residual polyethylene glycol in the composition acted as a humectant adversely affecting the capsule.

Table 2 provides an exemplary formulation for a ribavirin composition having approximate percent range of particular ingredients.

TABLE 2

| Formulation Ingredient | % Total Formulation (wet)[1] | Function in the Formulation |
|---|---|---|
| ribavirin, USP | 41-67 | Active Pharmaceutical Ingredient |
| microcrystalline cellulose | 24-33 | Binder/Diluent |
| croscarmellose sodium | 2-6 | Disintegrant |
| povidone | 1-4.5 | Binder |
| lactose | 5-10 | Diluent |
| water U.S. Pat. No. | 15-79 | Wetting Agent[2] |

[1]Calculated on a wet basis by weight.
[2]The wetting agent is removed from the formulation.

Under another embodiment of the present invention, the dry ingredients listed in the Table 2 above are mixed together and granulated with the wetting agent. The granulated mass can then be extruded through a screen (0.4 mm -1.0 mm), spheronized, and fluid bed dried.

One of the preferred embodiments results in a product that is encapsulated in size "1" or "1el" (elongated) capsules to form a 200 milligram ("mg") dose of active ribavirin. The total capsule weight is approximately 270 mg (excluding the capsule shell). One of the preferred embodiments also calls for a 200 mg pharmaceutical dosage in which at least 90% of the ribavirin dissolves within 30 minutes.

In an embodiment of the present invention, a ribavirin composition can contain from about over 70 wt % ribavirin, about 5-25 wt % microcrystalline cellulose, about 1-10 wt % croscarmellose, about 0.5-5 wt % povidone, about 1-15 wt % lactose, or the pharmaceutically acceptable salts or hydrates thereof. Water can be added in an amount of from about 50-80 wt % of the dry ingredients to granulate the mixture. Table 3 provides examples of ribavirin compositions having approximate percent ranges of particular ingredients and the ingredients for the preparation of a batch of capsules filled with the composition.

TABLE 3

Ribavirin Capsules and ingredients thereof.

| Ingredient | Ingredient[1] | Capsule 200 mg of ribavirin[1] | 10,000 Capsules of 200 mg (size 1el)[2] | 10,000 Capsules 300 mg (size 0) | 1,00,000 Capsules 200 mg (size 1el) | 1,00,000 Capsules 400 mg (size 00) |
|---|---|---|---|---|---|---|
| ribavirin USP | 74% | 200 mg | 2 kg | 3 kg | 200 kg | 400 kg |
| microcrystalline cellulose | 15.6% | 42 mg | 0.42 kg | 0.63 kg | 42 kg | 84 kg |
| croscarmellose sodium | 3.7% | 10 mg | 0.1 kg | 0.15 kg | 10 kg | 20 kg |
| povidone | 1.1% | 3 mg | 0.03 kg | 0.045 kg | 3 kg | 6 kg |
| Lactose | 5.6% | 15 mg | 0.15 kg | 0.23 kg | 15 kg | 30 kg |
| water USP | | | 1.75 kg | 2.63 kg | 165 kg | 330 kg |
| Total[3] | 100% | 270 mg | 2.7 kg | 4.05 kg | 270 kg | 540 kg |
| Total with Water USP | | | 4.45 kg | 6.68 kg | 435 kg | 870 kg |
| % Water USP in the wet granulation[4] | | | 39 | 39 | 38 | 38 |
| % of Water USP to dry ingredients[5] | | | 65 | 65 | 61 | 61 |

[1]Calculated on a dry basis. The water is removed.
[2]The amounts (in kilograms) of the listed ingredients are provided for the preparation of a ribavirin composition used to fill 10,000 capsules of 1el size to provide a 200 mg ribavirin dose per capsule.
[3]The amounts listed in this row reflect the total amount of dry ingredients, i.e., the total excluding water.
[4]This is the weight percent of water added to the mixture calculated on a wet basis.
[5]This row provides the percent ratio of added water to the dry ingredient (derived by dividing the amount of water over the total amount of dry ingredients).

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Example 1

Free flowing ribavirin particles can be prepared by the following general procedure. Ribavirin USP (about 5820 g) was blended with microcrystalline cellulose (about 1230 g), lactose monohydrate (about 440 g), croscarmellose sodium (about 291 g), and povidone (about 87 g). Purified water (about 3700 g), was added to the mixture with stirring to wet granulate the mixture. The composition was then dried and milled. Croscarmellose sodium (about 1% of the dried milled granules) together with magnesium stearate (about 0.75% of the dried milled granules) was then added to the dried, milled particles for lubrication. The angle of repose of this composition was determined to be no higher than about 35 degrees.

Example 2

Ribavirin compositions can be prepared in the form of uniformly sized pellets by the following general procedure. Ribavirin USP is mixed for about 3 to about 15 minutes along with microcrystalline cellulose, lactose monohydrate, croscarmellose sodium and povidone in a suitably sized granulator. For example, a TK Fielding mixer can be used operating at 200 RPM for three minutes to mix a suitably sized batch of dry ingredients. Purified water USP is added to the mixture at a rate of about 2 kg to about 50 kg per minute. The wet mass is granulated for about an additional 30 seconds to about 20 minutes depending on batch size. The wet granulation can be carried out in the same TK Fielding mixer thereby minimizing loss on transfer.

After granulating, the wet mass is fed into an extruder at a rate that avoids product stagnation and excessive accumulation. For example, a twin dome extruder can be employed such as a Fuji Model TDG-110P available from LCI. The extrudate from the extruder can be any where from about a quarter to about three inches in length. The extruded mass is spheronized on an appropriately sized marumerizer or equivalent equipment using parameters that would produce highly uniformed sized pellets. Typical parameters used during said spheronization include those listed as follows:

| | |
|---|---|
| Jacket water temperature | 45-60° C. |
| Groove plate configuration | Medium |
| Marumerizer speed setting | 0.5-1.0 |
| Spheronization time | 0.5-2 minute/portion |

Common spheronizers can be used as, for example, a Fuji Marumerizer Model QJ-700VH available from LCI Corporation. This spheronizer can be used to make uniformly sized pellets. For example, using 5-10 kg of an extruded ribavirin composition, the spheronizer when run at about 400-600 RPMs for about 15 seconds to about 5 minutes to forms a narrow distribution with respect to the size of the pellets. Other examples include using a 7 kg batch running the spheronizer at about 500-600 RPMs for two minutes or using a 10 kg batch and running the spheronizer at about 500 RPMs for about 1 and ½ minutes.

The spheronization process forms wet pellets that are then dried, as by a fluid-bed drier. Drying is continued until the pellets have a loss on drying (LOD) of not more than about 5% and not less than about 0.5% is achieved.

Any fluid bed drier can be employed to dry these pellets. In an embodiment of the present invention, a fluid bed drier is set to have an inlet air temperature of about 70° C., an air volume of about 3000-5000 cfm, a shake duration of about 10 seconds and a shake interval of about 2 minutes and an inlet air dew point of about 8-15° C. Following drying, the pellets are sieved by use of a 16 mesh or 18 mesh screen or similar sized screen.

The pellets according to embodiments of the invention can be used to manufacture capsules, in which at least 90% of the ribavirin dissolves in 30 minutes. Additional ribavirin dosages having a different dissolution profile are also contemplated and achieved according to the teachings of the present invention. The dissolution profile can be further modified by the addition of coatings to the dried pellets to yield delayed- or sustained-release dissolution profiles. Coatings in common use include polymethacrylic materials, diethyl-aminophenyl materials, polyethylene glycols and other excipients, as well as other materials known in the art.

After the pellets are sieved, they can be coated by a relatively water insoluble material or film. This can be done by liquid phase microencapsulation, as is known in the art. The relatively non-water soluble material acts as a barrier coating the pellets. The release rate of the active in the composition of this coated pellet can be increased or decreased by the amount of coating on the pellets. Several polymers can be used for coating the pellets including cellulose acetate, ethyl cellulose, cellulose acetate phthalate, hydroxypropylmethyl cellulose acetate phthalate, etc. Practically any film forming polymer being insoluble in aqueous medium can be used for the preparation of the coatings on the pellets. Microencapsulation can be carried out with the aid of any suitable microencapsulating process, as known in the art, which is capable of forming a uniform continuous coating on the surface of the pellets.

Example 3

The following is a description of a representative manufacturing process for a 54-kg batch size of ribavirin pellets by wet granulation. A portion of the composition is initially prepared by weighing and transferring the following inactive ingredients into a 65-L PMA mixer: ca. 8 kg Ribavirin, USP; ca. 1.68 kg microcrystalline cellulose (Avicel PH101); ca. 0.6 kg lactose monohydrate; ca. 0.4 kg croscarmellose sodium (Ac-Di-Sol); and ca. 0.12 kg Povidone, PVP K30. This portion is then dry mixed in the 65-L PMA mixer for 3 minutes with the impeller and chopper running.

This mixture is then wet granulated by spraying ca. 7 kg of pressurized Purified Water, USP into the mixer. At the conclusion of the spraying, continue mixing with the impeller and chopper running for an additional 30 seconds. Mixing continues until proper granulating wetness is achieved. If proper wetness is not achieved, additional Purified Water USP is added to the mixer with the impeller running at about the same pressure. At the conclusion of the addition of any extra water, mixing is continued with the impeller and chopper running for an additional 30 seconds. The mixture is then ready to be discharged into a suitable container. These steps can be repeated for addition portions. In this example, the above steps were repeated five times to produce a 54 kg batch of product.

The next steps involve extrusion and spheronization of the combined portion. It is preferable to ensure that all product is removed from the 65-L PMA mixer and begin adding a portion of the granulated mixture into the hopper of a ADG-105 extruder. Extrusion is commenced with a target auger setting of 0.8, dome die size of 0.6 mm, and a spacer distance of 1.0 mm to form an extrudate. While the portion is being extruded, spheronize portions of ca. 2 kg using an LCI marumerizer with a target speed setting of 0.7 and a target spheronization time of 1 minute/2 kg.

The manufacturing parameters for the formulation have proved to be very rugged. The particle size distribution, however, is effected by the amount of water added in the granulation step. A wet mass moisture of approximately 40-42% by weight produces pellets having at least 98% of the pellets less than about 1200 microns and 92% greater than about 250 microns. This is a desirable result for particle size distribution. It should be noted that dry mass blending should be done with enough speed and time to ensure a uniform blend. As the dry powders are wetted, the impeller speed needs to be fast enough to produce a slow roping action. In past experience, the wet mass appeared almost over wet. However, the liquid addition during the granulation step should not stop until there is evidence of balls forming, i.e., evidencing true over wetness. The extruder speed should also be set so that there is no screen binding or lengthy strands of the extrudate produced.

Figure 1:
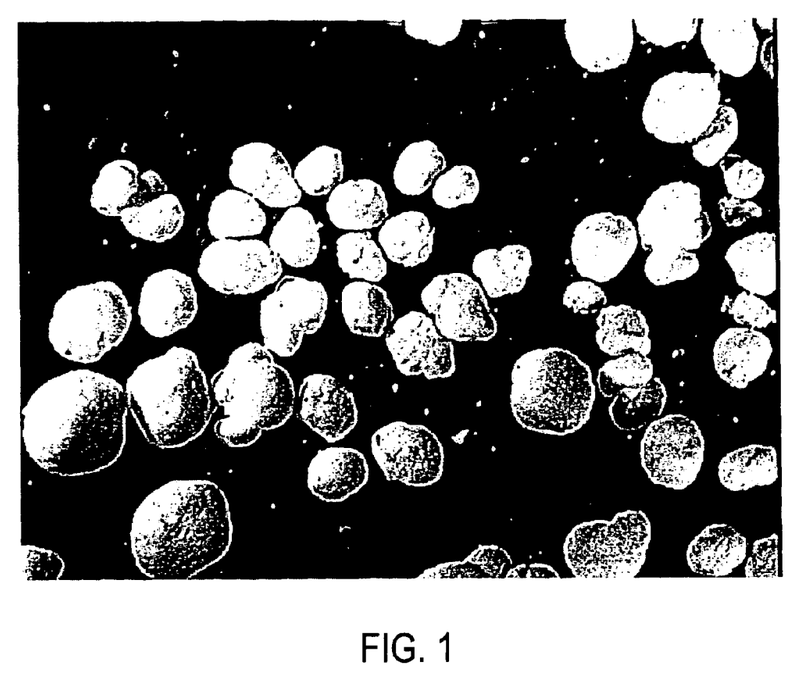
FIG. 1 is an optical photomicrograph of a ribavirin sample made by a wet granulation, spheronization process prior to any coating on the particles.

Spheronized pellets are then collected in the granulator/dryer bowl for drying, as in a WST-30 fluid-bed dryer. Pellets are then dried in equal portions until a target LOD of 0.2-2.0% is achieved. The dried pellets are transfer into a Russell sieve equipped with a 16-mesh screen and all product retained on the 16-mesh screen were rejected. An optical photomicrograph of a sample of the dried pellets was taken with a magnification of 10× and is shown in FIG. 1.

Example 4

Two commercial 202.5 kg batches of ribavirin pellets were prepared. Each batch of ribavirin pellets was prepared in the same manner as described in Example 3 except bulk ribavirin was also passed through a screen, e.g., a 12-6 mesh screen, prior to the wet granulation step. Further, the amounts of the individual ingredients were scaled-up and equivalent equipment was used that could accommodate the increased load of ingredients. In this example six portions of a ribavirin mixture was prepared each weighing 33.75 kg for each 202.5 kg batch. Approximately 19.5 kg of water was added to each 33.75 kg portion (i.e. a ratio of added water to powder blend of about 0.58 to about 0.65).

Example 5

Angle of repose data was collected for ribavirin composition made in accordance with Examples 1 and 3 and compared to bulk ribavirin and a commercial ribavirin product. In determining the angle of repose for the compositions of the present invention and comparative examples thereto, a sample was passed through a 12 mesh screen to break up agglomerates. The sample was then introduced into a stainless steel funnel with a 1 cm aperture/opening and passed through the funnel onto a clean sheet of white paper. Sample feeding was stopped when the height of the sample reached the lowermost part of the funnel. The funnel height was then measured, as well as the diameter (width) of the sample. With respect to the latter, the diameter of the mound of sample on the paper was averaged in two dimensions, x and y. The angle of repose for a given sample was calculated by taking the inverse tangent of the following equation: $\tan(a) = 2H/W$, where H is the height of the funnel from the paper and W is the averaged diameter of the poured sample at its base.

TABLE 4

Angle of Repose Data

| Sample | Mfr./Lot | Repose Angle Trial 1 | Trial 2 |
|---|---|---|---|
| Bulk Ribavirin USP[a] | Star Lake LW020204 | 44 | 42 |
| Rebetol[b] Commercial Capsules (test sample emptied from 70 capsules) | Schering Corp. 1RCJ315 | 42 | 44 |
| Ribavirin Particles prepared according to Example 1 | lot 3H6022 | 34 | — |
| Ribavirin Particles prepared according to Example 1 | lot 3H6023 | 34.8 | — |
| Ribavirin Particles prepared according to Example 1 | lot 3H6024 | 35 | — |
| Ribavirin Pellets prepared according to Example 3 | lot 3B1778 | 30 | 30 |
| Ribavirin Pellets prepared according to Example 3 | lot 3B1867 | 31 | 30 |
| Ribavirin Pellets prepared according to Example 3 | lot 1889 | 27 | 29 |

[a]It was difficult to assess an accurate angle of repose for bulk ribavirin due to its propensity to clumped together, which impeded its flow through the funnel. The angle of repose is likely higher than the measured value. No screening or sieving helped its flow.
[b]Rebetol is a commercial ribavirin composition from Schering Corp. Seventy 200 mg-strength ribavirin capsules were emptied and their contents combined and measured to determine their angle of repose.

As shown in Table 4 above, a process that includes the addition of water to a ribavirin mixture results in a ribavirin composition having superior free flowing characteristics relative to ribavirin itself and ribavirin compositions from a commercial source.

Example 6

The ribavirin composition can be made in accordance with embodiments of the present invention having a highly uniform particle distribution. The following table shows the sieve analysis of a manufactured batch according to Examples 3 and 4. As shown in the table below, the distribution particle size is highly uniform with over 90 wt % of the particles being at least 250 μm (i.e. less than 10% of the particles pass through a 60-mesh sieve).

TABLE 5a

Sieve Data Summary

| Sieve No. | Average wt % Retained Example 3 | Average wt % Retained Example 4 |
|---|---|---|
| 25 | 37 | 22-25 |
| 30 | 15 | 12-14 |
| 40 | 33 | 28-30 |
| 60 | 14 | 28-25 |
| 100 | 0.6 | 6-9 |
| 200 | 0 | 0.4-0.9 |
| Fines | 0 | 0-0.1 |

TABLE 5b

Sieve Data Summary

| Sieve Size (μm) | Differential wt % Greater than Indicated Size | Cumulative wt % Greater than Indicated Size |
|---|---|---|
| 710 | 35.78 | 35.78 |
| 600 | 22.12 | 57.90 |
| 425 | 28.34 | 86.24 |
| 250 | 12.05 | 98.59 |
| 150 | 0.14 | 98.43 |
| 90 | 0.70 | 99.13 |
| 53 | 0.0 | 99.13 |

Example 7

Pellets prepared in accordance with Examples 3 and 4 were used to fill several thousand size-1 capsules using an encapsulating machine. Sample capsules were collected throughout the encapsulation process and individual weights were determined. The weight variation among samples was determined in accordance with the procedures set forth in USP 26, Monograph <905> Uniformity of Dosage Units (2003). The capsule weight variation data is summarized in the table below.

TABLE 6

Uniformity of Weight Data

| Example | Sampling intervals | No. of capsules weighed (n) | Average Wt (mg) | Minimum Wt (mg) | Maximum Wt (mg) | % Wt variation |
|---|---|---|---|---|---|---|
| 3 | 12 | 120 | 269.5 | 258.0 | 287.6 | +/−6.5 |
| 4 | 27 | 864 | 272.1 | 251.8 | 286.9 | +/−6.7 |
| 4 | 28 | 896 | 269.6 | 254.2 | 283.1 | +/−5.9 |

An acceptable criteria for individual capsule fill weight is within +/−10%. Capsules manufactured with ribavirin compositions made according to embodiments of the present invention have fill weights within +/−8%, e.g., within about +/−7%.

Example 8

Capsules prepared in accordance with Example 7 were also tested for the capsule's content uniformity. Sample capsules were collected throughout the encapsulation process for the content uniformity test. Content uniformity assays of ribavirin were preformed on 3 capsules from each sampling interval for a total of 36 assays for capsules made with the composition of Example 3 and 30 assays for capsules made with the composition of Example 4. The content uniformity was determined in accordance with the procedures set forth in USP 26, Monograph <905> Uniformity of Dosage Units (2003). The data are summarized in the table below.

TABLE 7

Uniformity of Ribavirin Content.

| Example | No. of capsules weighed (n) | Average (%) | Minimum (%) | Maximum (%) | RSD (%) |
|---|---|---|---|---|---|
| 3 | 36 | 98.3 | 95.5 | 103.0 | 1.9 |
| 4 | 30 | 98.1 | 84.6 | 102.2 | 3.7 |
| 4 | 30 | 99.9 | 85.3 | 104.1 | 3.2 |

As shown in the table above, the average content of ribavirin in any given capsule is no less than about 98%. Moreover, the standard deviation is less than about 3% or 4%. The above table is indicative of the high content uniformity that can be achieved in practicing certain aspects of the present invention. The high ribavirin content uniformity can advantageously be achieved in commercial sized batches, as shown for the results of Example 4 in Table 7, e.g., a ribavirin content of between about 85% and 105%.

As a comparison, capsules prepared with the composition of Example 3 were compared to a commercial 200 mg ribavirin capsule with the following results.

| Potency Assay (Content Uniformity (20 capsules) | |
| --- | --- |
| Test Product Lot: | 98.4% (1.5% RSD) |
| Reference Product Lot: | 98.3% (5.7% RSD) |

Example 9

Dissolution Profiles

Capsules containing the ribavirin composition made in accordance with Example 3 were tested to determine their dissolution profiles. Twelve capsule were tested in accordance with the procedures set forth in USP 26, Monograph <711> Dissolution (2003). The dissolution profiles for a ribavirin, 200-mg capsule, are shown in Table 8.

TABLE 8

Results of In Vitro Dissolution of uncoated pellets

| Sampling Times | Test Product Made according to Example 3 Strength: 200 mg | | |
| --- | --- | --- | --- |
| (min) | Mean (%) | Range (%) | % RSD (n = 12) |
| 15 | 97.2 | 5.8 | 1.74 |
| 30 | 97.7 | 4.7 | 1.48 |
| 45 | 96.5 | 5.2 | 1.66 |
| 60 | 96.2 | 3.9 | 1.27 |

Figure 2:
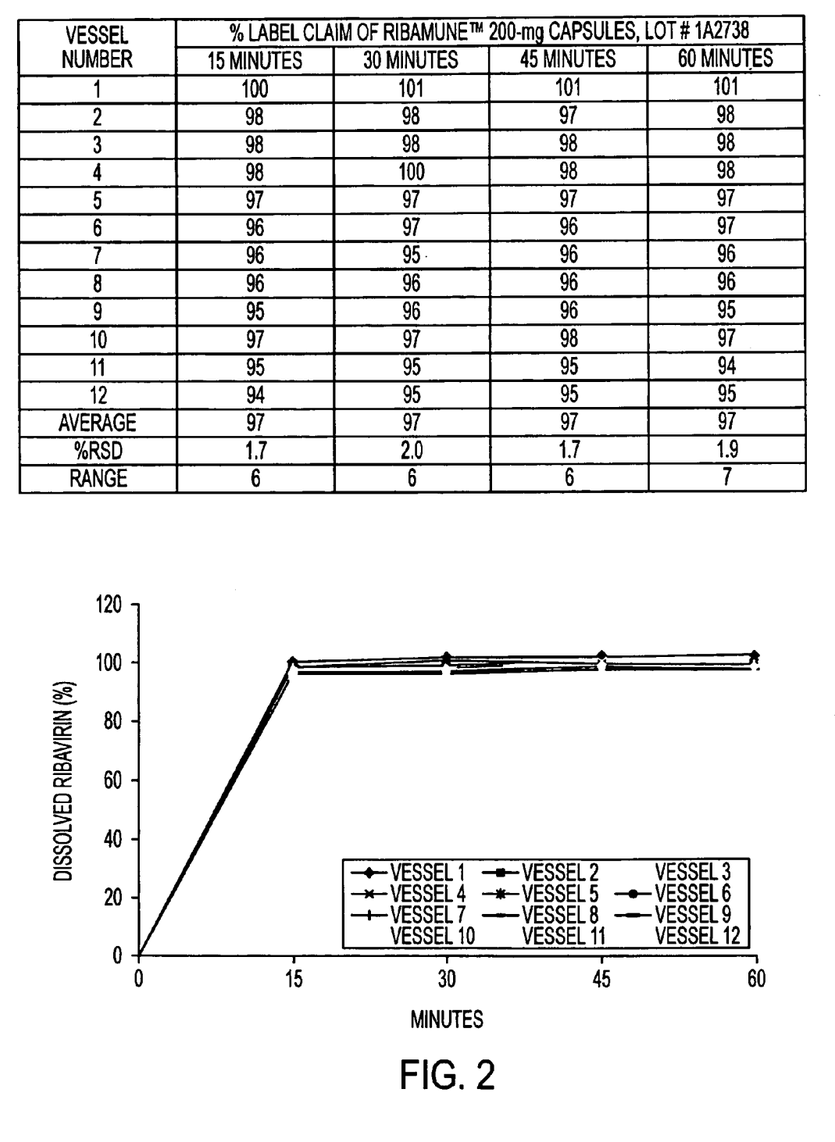
FIG. 2 is a chart showing the dissolution profile of a 200 mg strength capsule containing an immediate release ribavirin composition and the data summarizing the dissolution profile.
Figure 3:
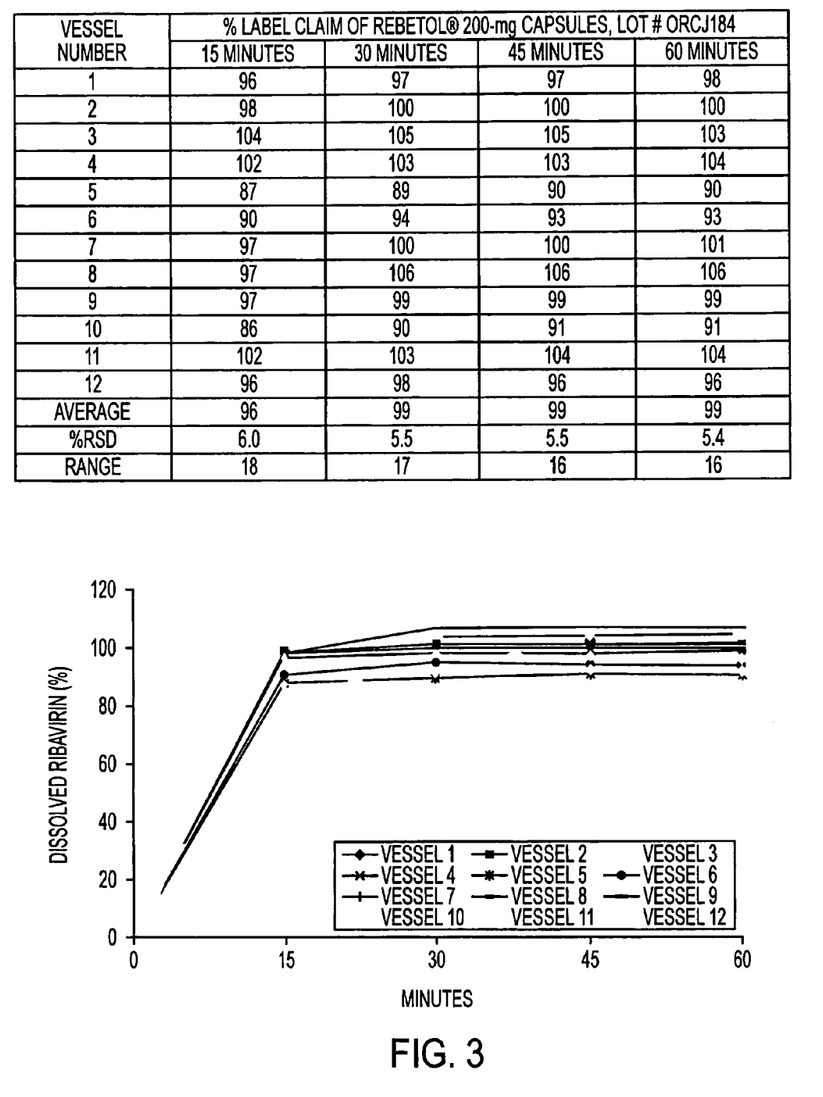
FIG. 3 is a dissolution profile showing a commercial, immediate release 200 mg strength capsule of ribavirin, which has a standard deviation of greater than 5.4%.

The uniform dissolution of a 200 mg ribavirin capsule manufactured from the composition of Example 3 is also shown in FIG. 2 and the accompanying information in the table of FIG. 2. As shown in FIG. 2, ribavirin dosages manufacture with ribavirin compositions prepared in accordance with embodiments of the present invention result in a standard deviation in the dissolution of no greater than 2%. The dissolution profile of a commercial 200 mg ribavirin capsule is shown in FIG. 3 along with accompanying data. As evidenced by comparing FIGS. 2 and 3, the dissolution consistency of ribavirin dosages prepared in accordance with embodiments of the present invention result in an improved immediate release ribavirin capsule.

The consistency in dissolution influences the bio-availability of ribavirin in a subject. The dissolution uniformity of the immediate release pellets of the present invention can be advantageously applied to a sustained release formulation. By coating these pellets or using the pellets in a coated tablet, sustained release product can be prepared with a high degree of control over the release rate of the drug.

In this disclosure there is described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A process of forming ribavirin particles, the process comprising:
   mixing ribavirin with at least one excipient to form a mixture;
   adding water to the mixture in an amount of from about 15 wt % to about 80 wt % based on the total weight of the mixture to form a wet granulated mixture; and
   drying the wet granulated mixture to form ribavirin containing particles.

2. The process according to claim 1, wherein the water is added at a rate of about 2 kg per minute to about 50 kg per minute.

3. The process according to claim 1, wherein said drying step comprises heating the wet granulated mixture to a temperature ranging from about 35° C. to about 45° C., until the particles contain a moisture content ranging from 0.5% to 5.0%.

4. The process according to claim 1 further comprising filling a plurality of capsules with the ribavirin containing particles wherein the plurality of capsules have a weight variability of within +/−8% and a ribavirin content with a standard deviation of less than about 4%.

5. The process of claim 1, further comprising spheronizing the wet granulated mixture prior to the drying step.

6. The process of claim 1, comprising mixing ribavirin with two or more excipients to form the mixture.

7. The process of claim 1, wherein the amount of water added to the ribavirin mixture is between about 50 wt % to about 80 wt % based upon the dry ingredients.

8. The process of claim 1, further comprising forming a dosage form from the ribavirin containing particles.

9. The process of claim 1, further comprising forming tablets from the ribavirin containing particles.

10. The process of claim 8, wherein the dosage form contains up to 1200 mg of ribavirin.

11. The process of claim 8, wherein the dosage form contains 400 mg to 600 mg of ribavirin.

12. The process of claim 1, further comprising filling a plurality of capsules with the ribavirin containing particles.

13. A process for preparing a ribavirin composition, the process comprising:
   mixing ribavirin with at least two excipients to form a mixture;
   adding water to the mixture in an amount of from about 15 wt % to about 80 wt % based on the total weight of the mixture to form a wet mixture; and
   forming a free flowing ribavirin composition from the wet mixture, wherein the composition has an angle of repose of no higher than about 35 degrees.

14. A process for preparing a free flowing granular ribavirin composition, the process comprising: wet granulating a ribivirin mixture by adding water in an amount of from about 50 wt % or more based on the weight of the mixture and drying the ribavirin mixture to form a free flowing ribavirin composition, wherein the ribavirin composition has an angle of repose no higher than about 35 degrees.

15. The process according to claim 13 wherein forming the free flowing ribavirin composition comprises spheronizing and drying the wet mixture.

16. The process according to claim 13 wherein forming the free flowing ribavirin composition comprises drying and milling the wet mixture.

17. The process according to claim 16 further comprising adding croscarmellose sodium and magnesium stearate to the dried, milled ribavirin composition.

18. The process according to claim 14 further comprising extruding and spheronizing the ribavirin mixture prior to drying the mixture.

19. The process according to claim 14 wherein the ribavirin composition has an angle of repose no higher than about 30 degrees.

20. The process of claim 1, wherein the mixture contains at least about 70% by weight of ribavirin.

21. The process according to claim 1 wherein ribavirin is mixed with at least one filler and at least one binder to form the mixture.

22. The process of claim 21, wherein the filler is selected from the group consisting of: lactose monohydrate and microcrystalline cellulose.

23. The process according to claim 1 wherein ribavirin is mixed with at least one filler, at least one disintegrant, and at least one binder to form the mixture.

24. The process of claim 1 wherein the mixing step comprises mixing at least about 70 wt % ribavirin with about 5-25 wt % microcrystalline cellulose, about 1-10 wt % croscarmellose, about 0.5-5 wt % povidone, about 1-15 wt % lactose, or the pharmaceutically acceptable salts or hydrates thereof to form the mixture.

25. The process according to claim 6 further comprising milling the dried ribavirin mixture to form the ribavirin containing particles.

26. The process according to claim 25 further comprising adding a disintegrant and a lubricant to the dried, milled ribavirin containing particles.

* * * * *